(12) United States Patent
Brandt et al.

(10) Patent No.: US 7,179,451 B2
(45) Date of Patent: Feb. 20, 2007

(54) HAIR STYLING COMPOSITIONS

(75) Inventors: Loralei Marie Brandt, Cary, IL (US); Paul Howard Neill, Hinsdale, IL (US); John Edward Wydila, Schaumburg, IL (US)

(73) Assignee: Unilever Home & Personal Care USA division of Conopco, Inc., Chicago, IL (US)

( * ) Notice: Subject to any disclaimer, the term of this patent is extended or adjusted under 35 U.S.C. 154(b) by 7 days.

(21) Appl. No.: 09/826,498

(22) Filed: Apr. 4, 2001

(65) Prior Publication Data

US 2001/0022967 A1 Sep. 20, 2001

Related U.S. Application Data

(63) Continuation of application No. 09/275,149, filed on Mar. 24, 1999.

(51) Int. Cl.
*A61Q 5/06* (2006.01)
*A61K 8/73* (2006.01)

(52) U.S. Cl. ............... 424/70.13; 424/70.1; 424/70.11; 424/70.15

(58) Field of Classification Search ............. 424/70.13, 424/70.15, 70.16, 70.1, 70.11, 70
See application file for complete search history.

(56) References Cited

U.S. PATENT DOCUMENTS

| 4,151,269 | A | * | 4/1979 | Torii et al. ................ 424/47 |
|---|---|---|---|---|
| 4,411,891 | A | * | 10/1983 | Mizutani et al. | |
| 5,085,859 | A | * | 2/1992 | Halloran et al. ............... 424/71 |
| 5,753,216 | A | * | 5/1998 | Leitch et al. ............ 424/70.12 |
| 5,804,166 | A | * | 9/1998 | Chan et al. ................... 424/47 |
| 5,833,968 | A | * | 11/1998 | Keil et al. ................ 424/70.17 |
| 5,985,294 | A | * | 11/1999 | Peffly ......................... 424/401 |
| 6,190,647 | B1 | * | 2/2001 | Karlen et al. | |
| 6,403,542 | B1 | * | 6/2002 | Maurin et al. .............. 510/122 |

FOREIGN PATENT DOCUMENTS

WO 95/00104 * 1/1995

OTHER PUBLICATIONS

"Specialty Product for Personal Care" J. Soc. Cosmet. Chem., 47, pp. 73-84, Mar./Apr. 1996.*
ISP Charst re Styleze™ CC-10, Product information, 26 pages, Sep. 1996.*
Research Disclosure, "A New Polymer for Hair Care Applications", pp. 317-322, May 1996.*
BASF Corporation, Technical Bulletin of Luviset® P.U.R., Dec. 1998.*

* cited by examiner

*Primary Examiner*—Sreeni Padmanabhan
*Assistant Examiner*—Gina C. Yu
(74) *Attorney, Agent, or Firm*—Karen E. Klumas

(57) ABSTRACT

The composition comprises: (a) less than about 1.5% active of one or more holding polymers, (b) one or more saccharides, having monomeric units greater than two, and (c) a carrier.

13 Claims, No Drawings

HAIR STYLING COMPOSITIONS

This is a continuation of Ser. No. 09/275,149 filed Mar. 24,1999.

FIELD OF THE INVENTION

The present invention is directed to hair conditioning and styling compositions and a method for styling the hair. The hair styling compositions have excellent styling, detangling, conditioning, and curl retention properties, and are washable from treated hair. In particular, the present invention relates to hair styling compositions comprising one or more holding polymers, and one or more saccharides such as oligosaccharide or polysaccharide, in a carrier, and a method of styling human hair.

BACKGROUND OF THE INVENTION

Normal hair can be fine, limp, and lacking in body such that hair does not hold a curl well. Furthermore, hair can lose body and be weakened as a result of chemical treatments, such as coloring and perming. Additionally, hair can be weakened further by other factors such as bleaching from the sun or chlorinated swimming pool water.

The condition and appearance of the hair can be improved by applying a hair styling composition that conditions and helps maintain the human hair in a particular predetermined hair configuration, hair set or hair style. Hair setting and conditioning can be achieved by applying the hair styling composition to the wet hair, fixing the hair by drying and by shaping or combing in order to achieve the desired hair shape or hair style. Similarly, after applying the composition to the hair, the wet hair can be set by using any of a variety of curlers or rollers to mechanically fix the hair in a predetermined configuration before drying. The wet hair can be dried either by ambient air drying, electrical drying, or hot air, (for example blow drying), to set the hair.

The problem encountered in hair styling is the tendency of human hair to return to its natural, or original, shape. For example, hair returns to its natural shape almost immediately if moistened. Similarly, high humidity conditions accelerate the tendency of human hair to return to its natural shape. Therefore, intensive efforts have been directed toward providing a hair set with sufficient holding power to maintain the desired hair shape until the next shampoo.

As indicated by the tendency of hair to return to its original shape, the hair style configuration resulting from setting the hair is reversible. However, the rate at which hair returns to its natural shape is dependent upon the method used to shape or set the hair. One example is a hair set performed with wet hair strands rolled tightly, either in curls around the finger or on curlers, followed by drying the hair and unrolling the curlers after drying. In this case, the release of the hair from the curlers brings about a deformation-causing load which tends to relax the curl. The hair style thus obtained can last for several days, but the hair style will not last if the hair is wetted or exposed to high humidity. In addition, natural forces combined with the weight of the hair will cause the hair to return to its original shape over time.

Investigators have sought to delay the combined action of natural forces and moisture that can cause hair to return to its original or natural shape by applying compositions containing polymers that assist the hair in retaining the desired hair configuration. When applied to hair from either aqueous or hydroalcoholic solutions, in the form of, for example, gels, mousses or hair sprays, the polymers form a film on the hair upon drying to help maintain the hair in the desired hair style configuration. The polymeric film promotes cohesion and gluing of the individual hair fibers, gives stability to the hair style, and may also act as a moisture barrier. The principal objective of a hair styling composition, therefore, is to coat the styled hair with a polymeric film that provides hair with rigidity, protects the hair style against humidity and wind, retain the hair style, and impart good feel and conditioning to the styled hair.

High concentrations of nonionic, cationic, amphoteric, and anionic holding or fixative polymers have been used in hair styling compositions. However, high concentrations of polymers have disadvantages such as high water solubility, low hydrophobicity, and low substantivity on hair fibers. Therefore, these high polymer concentrations will generate flaking due to easy elimination of the polymer from the hair by combing and brushing. As a result, investigators have continued to search for compounds and compositions that provide the benefits of improved durability, humidity resistance, and feel of the hair, while conditioning the hair and minimizing flaking.

The disadvantages attributed to high concentrations of traditional vinyl and acrylic polymers has led investigators to search for new hair styling polymers or new ways to overcome the disadvantages associated with these polymers. It would be desirable to provide a styling composition that will overcome the disadvantages associated with traditional polymers, that will impart good hair style and a natural feel to the hair, that will retain the hair set, and that will condition the hair.

It is the objective of the present invention to provide a hair styling composition, having lower concentrations of hair styling polymers, that impart excellent stiffness and crust signal, while at the same time, minimizing poor curl retention, poor hair feel, and flaking.

BRIEF SUMMARY OF THE INVENTION

The present invention is directed to hair styling compositions and a method of setting human hair that provides a long lasting hair style while minimizing tackiness, stickiness and flaking. The composition generally contains: (a) less than about 1.5% active of one or more fixative holding polymers such as an anionic, cationic, amphoteric or nonionic polymer, (b) one or more saccharides, having monomeric units greater than two, such as oligosaccharides or polysaccharides, and (c) a carrier such as water or water/alcohol.

DETAILED DESCRIPTION OF THE INVENTION

Hair styling compositions of the invention include product forms such as mousse, hair serum, gel, pommade, hair spray, foam, creme, styling conditioner, etc. Unless otherwise indicated, the starting materials used to prepare the hair styling compositions of the present invention are either known or can be prepared according to known methods. Unless otherwise indicated, hair care compositions of the invention can be prepared by known methods or by methods analogous to known methods, such as simple mixing.

Unless otherwise indicated, as used herein percent (%) is weight percent. Unless otherwise indicated, as used herein ratio is weight ratio. The words holding polymer and polymer are defined as macromolecules built up by linking together smaller molecules or monomers. The word saccharide means oligosaccharide or polysaccharide having greater than two monomer units.

The hair styling composition generally includes at least one saccharide and at least one holding polymer. The hair styling compositions provide superior high humidity curl retention at ratios of saccharide to holding polymer from about 0.1:1.0 to about 2.2:1.0, preferably from about 0.1:1.0 to about 1.25:1.0, and most preferably at a ratio of about 0.7:1.0.

The holding polymer and saccharide combinations are particularly useful in hair styling compositions because the combinations are soluble in aqueous or hydroalcoholic mixtures, as well as in a range of acid to basic aqueous solutions. The hair styling compositions impart improved feel and conditioning to the treated hair, have improved set retention, and display little or no flaking.

A less heavy coating of polymer is used to hold the hair style, therefore the hair will retain more of its natural body, imparted body or stylability.

Another advantage of the compositions described herein is the ease of washability. It is believed that the combination of holding polymer and saccharide helps to retain the desirable properties of each component, and still allow a desired degree of stiffness with very natural, smooth and non-sticky feel. Lowered levels of holding polymer in combination with the saccharide will increase the washability and removability of the styling product from the hair thereby preventing unwanted build-up.

The hair styling compositions of the present invention impart good hairstyle retention and a smooth, natural feel to treated hair. The hair styling compositions are easy to apply to wet or dry hair, and also detangle and condition the hair. Quite surprisingly, combinations of holding polymer and saccharide were found to have superior curl retention at high relative humidity, that is, the mechanical properties of the dried hair styling composition do not appear to be seriously affected by the absorption of moisture from the air.

Yet another advantage of the present invention is to overcome stickiness and tackiness on the hair and hands, while imparting a smooth, natural feel to the hair. We have found that curl retention ability in the present invention does not occur with saccharides having two or less monomer units. Preferably, the saccharides have greater than 55 monomer units. In U.S. Pat. No. 5,833,968 Keil, W. et al. claims the use of disaccharide (two monomer units). However, when disaccharides are used, a great deal of stickiness or unnatural feel results (see Table 9).

The present invention also relates to a method for styling and setting the hair which comprises applying the hair styling composition to the hair, either before, or after, the hair is set. Actual methods of styling and setting the hair are the same as those methods conventionally performed with known styling and setting aids. Surprisingly, the hair styling aids of the invention have the enhanced properties described above. The viscosity of the hair styling composition does not appear to affect the enhance properties provided by the invention.

The holding polymer is present in the hair styling compositions of the invention from about 0.04% to less than about 1.5% active, or more preferably from about 0.04% to about 1.25% active. Most preferably, the holding polymer is present in the compositions of the invention from about 0.1% to about 1.25% active. The saccharide is present in the compositions of the invention from about 0.01% to about 50%, or more preferably from about 0.1% to about 25%. Most preferably, the saccharide is present in compositions of the invention from about 0.1% to about 10%.

Preferred holding polymers of the present invention include vinyl and acrylic-based resins such as Copolymer 845, 937 and 958, a vinyl pyrrolidone/dimethylaminoethyl methacrylate copolymer, Styleze CC-10, a PVP/DMAPA Acrylates Copolymer, Polymer 1189 (Terpolymer of Vinyl pyrrolidone/Vinyl Caprolactam and 3-(N-Dimethylamino-propyl) Methacrylamide, all of which are available from International Specialty Products; Gafquat polymers 734 and 755N designated as Quaternium-23, Gantrez ES425 is the butyl ester of PVM/MA copolymer, all supplied by International Specialty Products, PVP K-30 to K-90, a polyvinylpyrrolidone of various molecular weights, obtained from BASF, Flexan 130, a Sodium Polystyrene Sulfonate, obtained from National Starch, Amphomer 28-4910, an Octylacrylamide/acrylates/butylamino methacrylate copolymer supplied by National Starch, Amphomer LV-71, Octylacrylamide/Acrylates/Butylaminoethyl Methacrylate Copolymer, Balance 0/55, a Methacrylate polymer, Versatyl42, an Acrylates/Octylacrylamide Copolymer, Resyn 28-2930 is VA/Crotonates/Vinyl Neodecanoate Copolymer and Lovocryl-47, an Octylacrylamide/Acrylates/Butylaminoethylmethacrylate Copolymer, Amaze Starch Polymer, all supplied by National Starch, Polyether Polyurethanes are available from Tyndale Plains Hunter, polyurethanes from IDPI, Luviset PUR polyurethanes from BASF, acrylates copolymers, acrylamide copolymers, acrylamide/sodium acrylate copolymer, acrylate/ammonium methacrylate copolymer, acrylate copolymers, acrylic/acrylate copolymers, acrylic esters and methacrylic esters copolymer, adipic acid/dimethylaminohydroxypropyl diethylenetriamine copolymer, adipic acid/ epoxypropyl diethylenetriamine copolymer, allyl stearate/VA copolymer, aminoethylacrylate phosphate/acrylate copolymer, ammonium acrylate copolymers, ammonium vinyl acetate/acrylate copolymers, AMP acrylate/diacetoneacrylamide copolymers, AMPD acrylate/diacetoneacrylamide copolymers, butylated PVP, butyl ester of ethylene/maleic anhydride copolymer, butyl ester of PVM/MA copolymer, calcium/sodium PVM/MA copolymer, corn starch/acrylamide/sodium acrylate copolymer, diethylene glycolamine/epichlorohydrin/piperazine copolymer, diglycol/cyclohexanedimethanol/Isophthalates/sulfoisophthalates AQ 55S polymer, diglycol/isophthalates/sulfoisophthalates copolymer AQ29S polymer, dodecanedioic acid/cetearyl alcohol/glycol copolymer, ethyl ester of PVM/MA copolymer, isopropyl ester of PVM/MA copolymer, Graft-copoly(diemthylsiloxane iso-butyl methacrylate), Graft-copoly (IBMA;MEFOSEA/PDMS), methacrylates/acrylates copolymer/amine salt, methacryloyl ethyl betaine/methacrylate copolymers, octylacryl-amide/acrylate/butylaminoethyl methacrylate copolymers, octylacrylamide/acrylate copolymers, phthalic anhydride/glycerin/glycidyl decanoate copolymer, phthalic/trimellitic/glycol copolymers, polyacrylamide, polyacrylamidomethylpropane sulfonic acid, polybutylene terephthalate, polyethylacrylate, polyethylene, polymethacrylamidopropyl trimonium chloride, polyquaternium-1, polyquaternium-2, polyquaternium-4, polyquaternium-5, polyquaterium-6, polyquaterium-7, polyquaternium-8, polyquaternium-9, polyquaternium-10, polyquaternium-11, polyquaternium-12, polyquaternium-13, polyquaternium-14, polyquaternium-15, polyquaternium-16, polyquaternium-24, polyquaternium-28, polyquaternium-37, polyquaternium-46, polyvinyl acetate, polyvinyl butyral, polyvinyl imidazolinium acetate, polyvinyl methyl ether, ethyl ester of poly (methyl vinyl ether/maleic acid, butyl ester of poly (methyl vinyl ether/maleic acid, PVM/MA copolymer, PVP, PVP/acrylates copolymer, PVP/dimethylaminoethylmethacrylate terpolymer, PVP/eicosene copolymer, PVP/ethyl methacrylate/methacrylic acid copolymer, PVP/hexadecane copolymer, PVP/VA copolymer, PVP/VA/vinyl propionate copolymer, PVP/vinyl acetate copolymer, PVP/vinyl acetate/itaconic acid copolymer, quaternium-23, shellac, sodium acrylate/vinyl alcohol copolymer, sodium carrageenan, starch diethylaminoethyl ether, stearylvinylether/maleic anhydride copolymer, sucrose benzoate/sucrose acetate isobutyrate/butyl benzyl phthalate copolymer, styrene/PVP copolymer, sucrose benzoate/sucrose acetate isobutyrate/butyl benzyl phthalate/methyl methacrylate copolymer, sucrose benzoate/sucrose acetate iso-butyrate copolymer, Tricontanyl PVP, vinyl acetate/crotonate copolymers, vinyl acetate/crotonic acid copolymer, vinyl acetate/butyl maleate/Isobornyl acetate copolymer, vinyl acetate/crotonic acid/methacryloxybenzophenone-1 copolymer, vinyl acetate/crotonic acid/vinyl neodecanoate copolymer, vinyl caprolactam/PVP/Dimethylaminoethyl methacrylate copolymer, and mixtures thereof.

Preferred saccharides of the present invention include nonionic or cationic saccharides such as cellulose ethers including methyl cellulose, carboxymethyl cellulose, hydroxy propyl methyl cellulose, hydroxyethyl cellulose, hydroxypropyl cellulose, and ethyl hydroxyethyl cellulose, dextrans obtained from Sigma, Kitamer PC, a chitosan carboxylate and Kytamer L, a chitosan lactate obtained from Amerchol, Gafquat HS-100, Polyquaternium-28 from International Specialties, polyquaternium4, polyquaternium-10, sodium alginate, agarose, amylopectins, amyloses, arabinans, arabinogalactans, arabinoxylans, carrageenans, gum arabic, cellulose derivatives such as methylcellulose, hydroxypropylmethylcellulose, hydroxyethyl cellulose, carboxymethylcellulose, carboxymethylguar gum, carboxymethyl(hydroxypropyl)guar gum, hydroxyethylguar gum, hydroxypropylguar gum, cationic guar gum, chondroitins, chitins, chitosans, cocodimonium hydroxypropyl oxyethyl cellulose, colominic acid [poly(N-acetyl-neuraminic acid], corn starch, curdlan, dermatin sulfate, furcellarans, dextrans, cross-linked dextrans known as dextranomer (Debrisan), dextrin, emulsan, flaxseed saccharide (acidic), galactoglucomannans, galactomannans, glucomannans, glycogens, guar gum, or hydroxyethylstarch, hydroxypropylstarch, hydroxypropylated guar gums, gellan gum, glucomannans, gellan, gum ghatti, gum karaya, gum tragacanth (tragacanthin), heparin, hyaluronic acid, inulin, keratan sulfate, konjac mannan, laminarans, laurdimonium hydroxypropyl oxyethyl cellulose, liposan, locust bean gum, mannans, nigeran, nonoxylnyl hydroxyethyl cellulose, okra gum, oxidized starch, pectic acids, pectins, polydextrose, potato starch, protopectins, psyllium seed gum, pullulan, sodium hyaluronate, steardimonium hydroxyethyl cellulose, raffinose, rhamsan, tapioca starch, welan, levan, scleroglucan, stachyose, succinoglycan, wheat starch, xanthan gum, xylans, xyloglucans, and mixtures thereof. Microbial saccharides can be found in the fourth edition of Kirk-Othmer *Encyclopedia of Chemical Technology*, Fourth Edition. Vol. 16, John Wiley and Sons, NY pp. 578–611, 1994. Complex carbohydrates can be found in the fourth edition of Kirk-Othmer *Encyclopedia of Chemical Technology*, Fourth Edition. Vol. 4, John Wiley and Sons, NY pp. 930–948, 1994.

The hair styling compositions of the present invention are in an aqueous or hydroalcoholic carrier. That is, the carrier of the hair styling compositions of the present invention is either water or a mixture of water and one or more alcohols selected from the group consisting of methanol, ethanol, n-propanol or isopropanol.

Compositions according to the present invention may further comprise one or more optional ingredients which are normally found in hair styling agents.

Thickeners can be utilized alone or in combination so long as the chosen thickeners are compatible with the hair styling composition. Thickeners can include, for example, Acrylic acid homopolymers under the Carbopol name from BF Goodrich, acrylates/C10–30 alkyl acrylate crosspolymer (Carbopol 1342, 1382, Pemulins TR-1 and TR-2 from BF Goodrich), Acrylates/Steareth-20 Itaconate Copolymer, Acrylates/Ceteth-20 Itaconate Copolymer, National Starch, Bentonite, PVM/MA Decadiene Crosspolymer from International Specialties Products, Acrylates/steareth-20 methacrylate copolymer, Acrysol ICS-1, Rohm and Haas Co., acrylamide/sodium acrylate copolymer, Hostacerin PN 73, Hoecsht AG., acrylate copolymer (Antil 208) supplied by Goldschmidt, acrylic acid/acrylonitrogens copolymer (Hypan SA-100H, SR-150H) supplied by Lipo, Acrylic/acrylate copolymer (Carboset5 514, 515, 525, XL-19, XL-19X2, XI-28, XL40, 526) supplied by BF Goodrich, Ammonium acrylates/acrylonitrogens copolymer (Hypan SS-201) from Lipo, Quaternium-18 Bentonite, Sodium salt of crosslinked poly(acrylic acid) under the tradenames PNC 430, PNC 410, PNC 400 from 3V, Stearalkonium Bentonite, Claytone, supplied by Southern Clay, Quaternium-18 Hectorite (Bentone 38), Stearalkonium Hectorite (Bentone 27) supplied by Rheox, acrylamide/sodium acrylate copolymer (Hostacerin PN 73) supplied by Hoechst, Poly(acrylic acid) known as Carbopol 400 series (BF Goodrich) or Aquatreat (Alco 3V), polyquaternium-18 (Mirapol AZ-1) from Rhone Poulenc, polyquaternium-27, polyquaternium-31, polyquaternium-37, trihydroxystearin (Thixcin from Rheox; Flowtone from Southern Clay), Dimethylaminoethyl methacrylamide and acrylamide copolymer (Salcare SC63 from Ciba Specialties), Acrylic polymer cationic thickening agents (Synthalen CR and its related compounds) from 3V Sigma.

Other thickeners and polymers can be found in the "The Encyclopedia of Polymers and Thickeners for Cosmetics," *Cosmetics and Toiletries*, Lochhead, R., pp. 95–138, Vol. 108, (May 1993).

Further optional components can include, for example: pH adjusting agents, viscosity and rheology modifiers, pearlescers, opacifiers, suspending agents, preservatives, coloring agents, dyes, proteins, herb and plant extracts, polyols and other moisturizing and/or conditioning agents.

Hair compositions of the invention can be prepared by known methods or can be prepared by methods which are analogous to known methods.

It is known that high concentrations of holding polymer will cause unsightly flaking of the polymer from the hair. We have found that concentrations of holding polymer less than about 1.5% active level will provide hair styling compositions without this negative attribute. For example, ISP Disclosure 38541 uses 1.5% active 1163 holding polymer which we found to have high flaking from the hair (see Table 8).

Embodiments of the present invention will now be further illustrated by reference to the following examples and tables.

The following examples were prepared to show the effect of various ratios of saccharide/holding polym r on curl retention as shown in Table 1.

|  | A | B | C | D | E | F |
|---|---|---|---|---|---|---|
| Ratio | 0.1:1.0 | 0.4:1.0 | 0.7:1.0 | 1.0:1.0 | 0.2:1.0 | 1.3:1.0 |
| Hydroxyethyl Cellulose | 0.125 | 0.500 | 0.875 | 1.250 | 0.250 | 1.625 |

-continued

|                      | A     | B     | C     | D     | E     | F     |
|----------------------|-------|-------|-------|-------|-------|-------|
| Polymer 1189 (40%)   | 3.125 | 3.125 | 3.125 | 3.125 | 3.125 | 3.125 |
| Water                | Qs    | qs    | qs    | qs    | qs    | qs    |

|                           | G       | H       | I       |
|---------------------------|---------|---------|---------|
| Ratio                     | 1.6:1.0 | 1.9:1.0 | 2.2:1.0 |
| Hydroxyethyl Cellulose    | 1.600   | 1.900   | 2.200   |
| Polymer 1189 (40%)        | 3.125   | 3.125   | 3.125   |
| Water                     | qs      | qs      | qs      |

Polymer 1189 (Terpolymer of Vinyl pyrrolidone/Vinyl Caprolactam and 3-(N-Dimethylaminopropyl) Methacrylamide) available from ISP; Deionized water.

Test 1—Method Of Curl Retention At 80% Relative Humidity and 25° C.
1. Tresses were wetted, treated with example product and wrapped around a pegboard.
2. Tresses were allowed to air dry in a humidity chamber at 65% relative humidity and 25° C.
3. Tresses were carefully unwrapped and placed into 80% relative humidity and 25° C.
4. Readings were taken at 0.25 hour and 6 hours.
5. Set retention was calculated by the formula: $[(L_o-L_t)/(L_o-L_p)]*100$, where $L_o$ is the original length of the tress, $L_t$ is the length of the tress at time t, and $L_p$ is the length of the wrapped tress on the pegboard.

Test 2—Method was Test 1 wherein the Hair was Dried Under a Hair Drier Rather than at Ambient Temperature.

TABLE 1

| Example | Viscosity (cps) | Test 1 0.25 hrs. | Test 1 6 hrs. | Test 2 0.25 hrs. | Test 2 6 hrs. |
|---------|-----------------|------------------|---------------|------------------|---------------|
| A       | <100            | NA               | NA            | 53.6%            | 31.4%         |
| E       | 1,000–2,500     | 84.5%            | 79.4%         | NA               | NA            |
| B       | 1,500–3,000     | 96.7%            | 91.7%         | 85.2%            | 72.1%         |
| C       | 3,000           | 97.6%            | 92.6%         | 97.8%            | 89.0%         |
| D       | >3000           | NA               | NA            | 98.3%            | 89.0%         |
| F       | >3,000          | NA               | NA            | 98.6%            | 96.9%         |
| G       | >3000           | 95.0%            | 83.8%         | NA               | NA            |
| H       | >3000           | 91.8%            | 83.3%         | NA               | NA            |
| I       | >3000           | 92.7%            | 80.1%         | NA               | NA            |
| Water   | ≈1              | 15.9%            | 9.9%          | NA               | NA            |

Test 1 (air dry) and Test 2 (hair dryer)
NA means not evaluated.
A higher % curl retention indicates stronger hold.

These hair styling compositions were found to be effective at preventing significant curl loss.

The following examples were prepared to test various ratios of dextran/holding polymer and the effect of the molecular weight of the dextran on percent curl loss. Molecular weight is an indication of the number of monomer units in the saccharide. In other words, the greater the number of monomer units, the greater the molecular weight. (Dextrans—microbial produced polyglucose saccharide available from Sigma Chemical Company). These examples appear in Tables 3 and 4.

|                          | J     | K     | L     | M     | N     |
|--------------------------|-------|-------|-------|-------|-------|
| Dextran 10,400 mw        | 0.875 |       |       |       |       |
| Dextran 19,500 mw        |       | 0.875 |       |       |       |
| Dextran 42,000 mw        |       |       | 0.875 |       |       |
| Dextran 69,000 mw        |       |       |       | 0.875 |       |
| Dextran 167,000 mw       |       |       |       |       | 0.875 |
| Dextran 260,000 mw       |       |       |       |       |       |
| Dextran 460,000 mw       |       |       |       |       |       |
| Dextran 2,000,000 mw     |       |       |       |       |       |
| Polymer 1189 (40%)       | 3.125 | 3.125 | 3.125 | 3.125 | 3.125 |
| Water                    | qs    | qs    | qs    | qs    | qs    |

0.7:1.0 ratio of saccharide/holding polymer

|                    | O     | P     | Q     | R     |
|--------------------|-------|-------|-------|-------|
| Dextran 460,000 mw | 0.625 | 1.250 | 1.875 | 2.50  |
| Polymer 1189 (40%) | 3.125 | 3.125 | 3.125 | 3.125 |
| Water              | Qs    | qs    | qs    | qs    |
| Ratio              | 0.5:1 | 1:1   | 1.5:1 | 2:1   |

Table 3 describes the molecular weight effect of dextran on percent curl loss at 80% humidity and 25° C. The % curl loss was determined by using the Test 1 method and the following calculation: $[(C1-C2)/C1]*100$, where C1 is the curl retention at time t1, C2 is the curl retention at time t2.

TABLE 3

| Example | Viscosity (cps) | % Curl Loss at 6 hrs |
|---------|-----------------|----------------------|
| J       | <100 cps        | 24.8%                |
| K       | <100 cps        | 13.5%                |
| L       | <100 cps        | 24.9%                |
| M       | <100 cps        | 15.9%                |
| N       | <100 cps        | 16.3%                |
| Water   | <100 cps        | 91.1%                |

A lower % curl loss indicates stronger hold.
0.7:1 ratio saccharide/holding polymer These hair styling compositions were found to be effective at preventing significant curl loss.

Table 4 describes the effect of various ratios of saccharide/holding polymer on curl retention.

TABLE 4

| Example | Test 1 at 0.25 hrs. | Test 1 at 6 hrs. |
|---------|---------------------|------------------|
| O (0.5:1) | 94.6%             | 89.5%            |
| P (1:1)   | 93.8%             | 89.9%            |
| Q (1.5:1) | 98.11%            | 95.1%            |
| R (2:1)   | 96.46%            | 95.4%            |
| Water     | 15.9%             | 9.9%             |

A higher % indicates stronger hold.

These hair styling compositions were found to be effective at preventing significant curl loss. Table 3 shows that these hair styling compositions enhanced curl retention. Table 4 shows that various ratios of dextran provided enhanced curl retention.

The following examples were prepared to show the effect of other saccharides on curl retention.

|  | S | T | U |
|---|---|---|---|
| Carboxymethyl cellulose | 0.875 | | |
| Hydroxymethyl cellulose | | 0.875 | |
| Modified Hydroxyethyl cellulose | | | 0.875 |
| Polymer 1189 (40%) | 3.125 | 3.125 | 3.125 |
| Water | qs | qs | qs |

Modified hydroxyethyl cellulose is available from Hercules/Aqualon.
0.7:1 saccharide/holding polymer Table 5 describes the effect of various saccharides on curl retention at 80% relative humidity and 25° C.

TABLE 5

| Example | Viscosity (cps) approx | Test 2 0.25 hrs. | Test 2 6 hrs. |
|---|---|---|---|
| S | 3,000 | 86.6% | 76.8% |
| T | 3,000 | 96.4% | 89.9% |
| U | 1,000–2,500 | 74.0% | 35.0% |

A higher % indicates stronger curl retention

These hair styling compositions were found to be effective at preventing significant curl loss.

The following examples were made in order to show that different holding polymers could be used in combination with one or more saccharides in the present invention. These examples appear in Table 6.

|  | V | W | X | Y |
|---|---|---|---|---|
| Polyether Polyurethane (40,000 mw) | 1.500 | | | |
| POLYMER 1163 (10%) methacrylamidopropyl dimethylamine-vinyl-pyrrolidone copolymer. | | 12.50 | | |
| Polymer 1189 (40%) | | | 3.125 | 3.125 |
| Hydroxyethyl Cellulose | 0.875 | 0.875 | 0.875 | 0.875 |
| Aminomethyl propanol | 0.100 | | | |
| Chitosan Lactate | | | 0.250 | |
| Water | qs | qs | qs | qs |

Polyether Polyurethanes are available from Tyndale Plains Hunter. Chitosan Lactate is available from Amerchol.

The styling properties with and without saccharide/holding polymer were tested below.

Test 3. Method for Assessing Curl Retention Using a Curling Iron
1. Tresses were shampooed with 1 ml Suave Strawberry Shampoo (available from Helene Curtis) for 60 seconds, rinsed for 30 seconds.
2. Excess water was squeezed out until hair was damp.
3. 0.5 g of gel or solution was applied, tresses were combed with a fine tooth comb twice, and were dried in a hair dryer for 30 minutes.
4. Tresses were next curled with a hot curling iron for 15 seconds, allowed to cool and evaluated.
5. Tresses were evaluated by feeling the tresses.

Table 6 describes the stiffness, initial hold, and ability of the hair to curl with a hot curling iron. Table 6 also shows that saccharide may be used in combination with many different holding polymers.

TABLE 6

| Example | Polymer Type(s) | Stiffness/Hold Increase | Increase in Curling |
|---|---|---|---|
| V | Nonionic | Yes | Yes |
| W | Cationic | Yes | Yes |
| Y | Cationic | Yes | Yes |
| X | Cationic | Yes | Yes |

The following examples were prepared to show that the combinations of saccharide and holding polymer had significantly more crust and stiffness wh n compared to either polymer or saccharide alone. These examples are found in Table 7.

|  | Z | AA | BB |
|---|---|---|---|
| Hydroxyethyl cellulose | 0.500 | | 0.500 |
| Polymer 1189 (40%) | | 1.250 | 1.250 |
| Water | Qs | qs | Qs |

Test 4. Treatment Method for Stiffness/Crust Evaluation
1. Tresses were shampooed with 1 ml Suave Strawberry Shampoo for 60 seconds followed by a 30 second rinse under 40° C. tap water.
2. Excess water was removed by running fingers down the tress until no drops were seen.
3. 0.5 g of gel or solution was applied, worked into the fibers ten times, and the tresses were combed twice.
4. Tresses were wrapped around curlers and dried in a hair dryer for 30 minutes.
5. Tresses were unwrapped carefully and set up in a panel.
6. Trained panelists were asked to numerically rank, from low to high, the perceived crust and stiffness of the tresses without disturbing bonding or gluing of each tress.
7. Deionized water tress (treated in the above manner) was used as a negative control.

Table 7 describes the stiffness properties of saccharide/holding polymer combination where the tresses w re simply ranked in order of increasing crust and stiffness signal. For example, a lower number indicates less crust while a higher number indicates more crust.

TABLE 7

| Example | Crust | Stiffness |
|---|---|---|
| AA | 1 | 1 |
| Z | 2 | 2 |
| BB | 3 | 3 |

A higher number indicates more crust and more stiffness.

Table 7 shows that combinations of saccharide and holding polymer had significantly more crust and stiffness when compared to either holding polymer or saccharide alone.

The following examples were prepared to evaluate flaking of the polymer from the hair. These examples are found in Table 8.

|  | CC | DD | EE | FF | GG |
|---|---|---|---|---|---|
| Hydroxyethyl cellulose | 0.5 | 0.84 | 1 | 1.2 | 1.2 |
| POLYMER 1163 (10%) methacrylamidopropropyl dimethylamine-vinylpyrrolidone copolymer. | 10.0 | 10.0 | 10.0 | 10.0 | 15.0 |
| Water | Qs | qs | qs | qs | qs |
| Ratio | 0.5:1.0 | 0.84:1.0 | 1.0:1.0 | 1.2:1.0 | 0.8:1.0 |

Test 5. Method to Evaluate Flaking
1. 0.5 g of material was applied to 2 g tress and combed through twice.
2. Tresses were allowed to dry undisturbed.
3. A small tooth comb was used to break the crust and flaking was visually categorized by panelists.
4. Flaking on the hair was determined from visual inspection of the tresses.

TABLE 8

| Example | Flaking |
|---|---|
| CC | None to Slight |
| DD | None to Slight |
| EE | None to Slight |
| FF | Slight to Moderate |
| GG | Moderate to High |

Example CC to FF are 1% active level.
Example GG is 1.5% active level.

Example CC, DD and EE show very little flaking. Example FF shows increased flaking. However, in example GG flaking becomes very problematic.

Keil et al. U.S. Pat. No. 5,833,968 used disaccharides in combination with various polymers. However, the disaccharides produced very tacky, sticky solutions which are undesirable on the hair.

The following examples were prepared to examine the crust and stickiness of several saccharides/holding polymer combinations. These examples appear in Table 9.

|  | HH | II | JJ | KK | LL |
|---|---|---|---|---|---|
| Sucrose | 3.0 | 7.0 | 3.0 | 7.0 |  |
| Hydroxyethyl cellulose |  |  |  |  | 0.56 |
| POLYMER 1163 (10%) methacrylamidopropropyl dimethylamine-vinylpyrrolidone copolymer. | 10.0 | 10.0 |  |  | 10.0 |
| Gafquat 755N (20%) |  |  | 2.50 | 2.50 |  |
| Water | qs | Qs | qs | qs | qs |
| Ratio | 3.0:1.0 | 7.0:1.0 | 6.0:1.0 | 14.0:1.0 | 0.56:1.0 |

TABLE 9

| Example | Crust (Rank) | Stickiness (Rank) |
|---|---|---|
| HH | 2 | 4 |
| II | 4 | 5 |
| JJ | 1 | 2 |
| KK | 3 | 3 |
| LL | 5 | 1 |

Attributes were ranked in increasing order (Low . . . High).

The disaccharide sucrose increased the tackiness and stickiness of the solution on both the hands and on the wet hair tresses. The stickiness was not apparent with the Hydroxyethyl cellulose (greater than 2 monomeric units) which is shown as example LL.

It should be understood that the present disclosure has been made only by way of preferred embodiment and that numerous changes in details of construction, combination and arrangement of parts may be resorted to without departing from the spirit and scope of the invention herein claimed.

We claim:

1. A hair styling composition comprising:
    (a) from about 0.04% to less than 1.5% active of a holding polymer;
    (b) hydroxyethyl cellulose; and
    (c) a carrier selected from the group consisting of methanol, ethanol, N-propanol, isopropanol, and a mixture thereof;
wherein the ratio of (a) to (b) is about 1:2.2 to about 1:0.4, and the holding polymer comprises a polymer which comprises a monomer combination of vinyl caprolactam, methacrylamidopropyl dimethylamine and vinylpyrrolidone.

2. A hair styling composition according to claim 1 wherein the ratio of (a) to (b) is about 1:0.4.

3. A hair styling composition according to claim 1 wherein the ratio of (a) to (b) is about 1:0.7.

4. A hair styling composition according to claim 1 wherein the ratio of (a) to (b) is about 1:1.

5. A hair styling composition according to claim 1 wherein the ratio of (a) to (b) is about 1:1.3.

6. A hair styling composition according to claim 1 wherein the ratio of (a) to (b) is about 1:1.6.

7. A hair styling composition according to claim 1 wherein the ratio of (a) to (b) is about 1:1.9.

8. A hair styling composition comprising:
    (a) from about 0.04% to less than 1.5% active of a holding polymer;
    (b) a nonionic dextran; and
    (c) a carrier selected from the group consisting of methanol, ethanol, N-propanol, isopropanol, and a mixture thereof;
wherein the ratio of (a) to (b) is about 1:2.2 to about 1:0.2, and the holding polymer comprises a polymer which comprises a monomer combination of methacrylamidopropyl dimethylamine and vinylpyrrolidone.

9. A hair styling composition according to claim 8, wherein the holding polymer comprises a polymer which comprises a monomer combination of vinyl caprolactam, methacrylamidopropyl dimethylamine and vinyl pyrrolidone.

10. A hair styling composition according to claim 1 wherein the holding polymer consists essentially of a polymer which comprises a monomer combination of vinyl caprolactam, methacrylamidopropyl dimethylamine and vinyl pyrrolidone.

11. A hair styling composition according to claim 8 wherein the holding polymer consists essentially of a polymer which comprises a monomer combination of methacrylamidopropyl dimethylamine and vinyl pyrrolidone.

12. A hair styling composition according to claim 1 wherein the holding polymer is present in the composition in an amount of from about 0.04% to about 1.25% active.

13. A hair styling composition according to claim 8 wherein the holding polymer is present in the composition in an amount of from about 0.04% to about 1.25% active.

* * * * *